United States Patent [19]

Tani et al.

[11] Patent Number: 4,637,994

[45] Date of Patent: * Jan. 20, 1987

[54] ADSORBENT AND PROCESS FOR PREPARING THE SAME

[75] Inventors: Nobutaka Tani, Minoo; Tsuneo Hayashi, Ashiya, both of Japan

[73] Assignee: Kanegafuchi Kagaku Kogyo Kabushiki Kaisha, Osaka, Japan

[*] Notice: The portion of the term of this patent subsequent to Mar. 18, 2003 has been disclaimed.

[21] Appl. No.: 737,880

[22] Filed: May 28, 1985

Related U.S. Application Data

[63] Continuation-in-part of Ser. No. 557,061, Dec. 1, 1983, Pat. No. 4,576,928.

[30] Foreign Application Priority Data

| Dec. 2, 1982 | [JP] | Japan | 57-212379 |
| Feb. 25, 1983 | [JP] | Japan | 58-31194 |
| Apr. 18, 1983 | [JP] | Japan | 58-68116 |
| Apr. 21, 1983 | [JP] | Japan | 58-70967 |
| Oct. 5, 1983 | [JP] | Japan | 58-187365 |

[51] Int. Cl.$^4$ .................................. B01J 20/22
[52] U.S. Cl. .................................. 502/404; 502/400; 502/401
[58] Field of Search ............... 502/400, 401, 402, 403, 502/404

[56] References Cited

U.S. PATENT DOCUMENTS

| 3,947,352 | 3/1976 | Cuatrecasas et al. | 502/404 X |
| 4,061,591 | 12/1977 | Oliver et al. | 502/403 X |
| 4,111,838 | 9/1978 | Schaeffer et al. | 502/404 X |
| 4,432,871 | 2/1984 | Yamawaki et al. | 502/401 X |
| 4,525,465 | 6/1985 | Someno et al. | 502/404 X |

Primary Examiner—W. J. Shine
Attorney, Agent, or Firm—Antonelli, Terry & Wands

[57] ABSTRACT

An adsorbent for removing low and/or very low density lipoprotein from body fluid in extracorporeal circulation treatment, which comprises a water-insoluble porous hard gel with exclusion limit of $10^6$ to $10^9$ daltons on which a sulfated compound is immobilized by a covalent linkage.

19 Claims, 3 Drawing Figures

ADSORBENT AND PROCESS FOR PREPARING THE SAME

CROSS-REFERENCE TO RELATED APPLICATION

This is a continuation-in-part of application Ser. No. 557,061 filed on Dec. 1, 1983, now U.S. Pat. No. 4,576,928.

BACKGROUND OF THE INVENTION

The present invention relates to a novel adsorbent and a process for preparing the same, more particularly, to an adsorbent for removing harmful substances to be removed from body fluid such as blood or plasma in extracorporeal circulation treatment.

There has been required a means for selectively removing harmful substances which appear in body fluid and closely relate to a cause or a progress of a disease. It is known that plasma lipoprotein, especially very low density lipoprotein (hereinafter referred to as "VLDL") and/or low density lipoprotein (hereinafter referred to as "LDL") contain a large amount of cholesterol and cause arteriosclerosis. In hyperlipemia such as familial hyperlipemia or familial hypercholesterolemia, VLDL and/or LDL show several times higher values than those in normal condition, and often cause arteriosclerosis such as coronary arteriosclerosis. Although various types of treatments such as regimen and medications have been adopted, they have limitations in effect and a fear of unfavorable side effects. Particularly in familial hypercholesterolemia, a plasma exchange therapy which is composed of plasma removal and compensatory supplement of exogenous human plasma protein solutions is probably the only treatment method being effective nowadays. The plasma exchange therapy, however, has various defects such as (1) a need for using expensive fresh plasma or plasma fractions, (2) a fear of infection by hepatitis viruses and the like, and (3) loss of all plasma components containing not only harmful components but also useful ones, i.e. in case of lipoprotein, not only VLDL and/or LDL but also high density lipoprotein (hereinafter referred to as "HDL") which is an important factor to prevent Arteriosclerosis are lost. For the purpose of solving the above defects, a selective removal of harmful components by a membrane and the like has been adopted. These methods, however, are insufficient in selectivity and cause a large loss of useful components from body fluid. There has been also tried a selective removal of harmful components by means of adsorption. For example, a synthetic adsorbent such as active carbon or Amberlite XAD (a registered trademark, commercially available from Rohm & Hass Co.) has been utilized for liver disease. Such an adsorbent however, has many defects such as poor selectivity and disability for removing high molecular weight compounds. Furthermore, for the purpose of increasing selectivity, there has been adopted an adsorbent based on the principle of affinity chromatography composed of a carrier on which a material having an affinity for a substance to be specifically removed (such material is hereinafter referred to as "ligand") is immobilized. In that case, however, it is difficult to obtain a sufficient flow rate for an extracorporeal treatment because a carrier is a soft gel such as agarose. Accordingly, a particular modification in column shape is required in order to obtain a large flow rate and the risk of an occasional clogging still remains. Therefore, a stable extracorporeal circulation cannot be achieved by the above method.

It is an object of the present invention to provide an adsorbent for selectively removing VLDL and/or LDL from body fluid such as blood or plasma in extracorporeal circulation treatment of hyperlipidemia.

A further object of the present invention is to provide a process for preparing the adsorbent.

These and other objects of the present invention will become apparent from the description hereinafter.

SUMMARY OF THE INVENTION

In accordance with the present invention, there can be provided an adsorbent for removing LDL and/or VLDL from body fluid in extracorporeal circulation treatment comprising a water-insoluble porous hard gel with exclusion limit of $10^6$ to $10^9$ daltons on which a sulfated compound is immobilized by a covalent linkage.

DETAILED DESCRIPTION OF THE INVENTION

Figure 1:
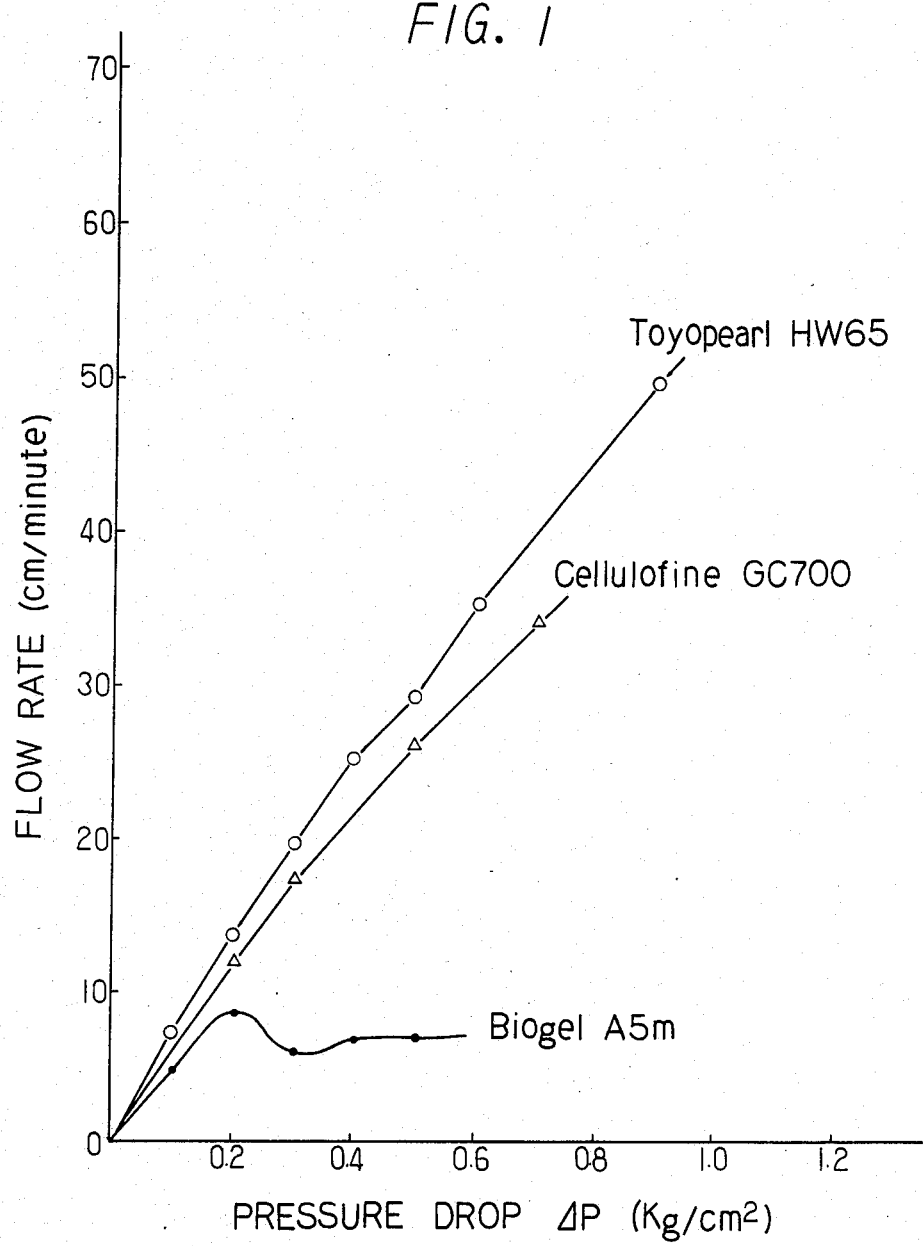
FIGS. 1 and 2 are graphs, respectively, showing relations between flow rate and pressure-drop obtained in Reference Examples 1 and 2.

It is suitable that carriers used in the present invention have the following properties:

(1) relatively high mechanical strength,
(2) low pressure-drop and no column clogging in case of passing body fluid through a column packed with a carrier,
(3) a large number of micro pores into which LDL and/or VLDL permeates substantially, and
(4) less change caused by a sterilizing procedure such as steam sterilization by autoclaving.

Therefore, the most suitable carrier used in the present invention is a water-insoluble porous polymer hard gel or a porous inorganic hard gel.

The porous hard gel used in the present invention is less swelled with a solvent and less deformed by pressure than a soft gel such as dextran, agarose or acrylamide.

The term "hard gel" and "soft gel" in the present invention is explained as follows:

A hard gel is distinguished from a soft gel by the following method described in Reference Examples 1 and 2. That is, when a relation between flow rate and pressure-drop is determined by passing water through a column uniformly packed with a gel, a hard gel shows a linear relationship while a soft gel shows a non-linear relationship. In case of a soft gel, a gel is deformed and consolidated over a certain pressure so that a flow rate does not increase further. In the present invention, a gel having the above linear relationship at least by 0.3 kg/cm$^2$ is referred to as "hard gel".

A pore size of the porous hard gel is selected depending on molecular weight, shape, or size of a substance to be removed, and the most suitable pore size may be selected in each case. For measuring the pore size, there are various kinds of methods such as mercury porosimetry and observation by an electron microscope as a direct measuring method. With respect to water-containing particles, however, the above methods some-times cannot be applied. In such a case, an exclusion limit may be adopted as a measure of pore size. The term "exclusion limit" in the present invention means the minimum molecular weight of a molecular which cannot permeate into a pore in a gel permeation chromatography (cf. Hiroyuki Hatano and Toshihiko Hanai: Zikken Kosoku Ekitai Chromatography (Experimental High-Pressure Liquid Chromatography), published by Kagaku Dojin). Phenomenally, a molecule having a molecular weight of more than exclusion limit is eluted near the void volume. Therefore, an exclusion limit can be determined by studying the relations between molecular weights and elution volumes using substances of various molecular weights in a gel permeation chromatography. An exclusion limit varies with a kind of substances to be excluded. In the present invention, an exclusion limit of the porous hard gel is measured by using globular proteins and/or viruses, and the preferable exclusion limit is $1 \times 10^6$ to $1 \times 10^9$. When the exclusion limit is more than $1 \times 10^9$, the adsorbing amount of LDL and VLDL decreases with a decrease of amount of immobilized ligand and a decrease of surface area, and further a mechanical strength of gel is reduced.

Removing VLDL and/or LDL being giant molecules having a molecular weight of more than $1 \times 10^6$, a porous hard gel having an exclusion limit of less than $1 \times 10^6$ is not practically available. On the other hand, a porous hard gel having an exclusion limit of from $1 \times 10^6$ to several million which is near a molecular weight of VLDL or LDL per se may be practically available to a certain extent. A preferable exclusion limit for removal of VLDL and/or LDL is $1 \times 10^6$ to $1 \times 10^9$, more preferably $1 \times 10^6$ to $1 \times 10^8$.

With respect to a porous structure of the porous hard gel used in the present invention, a structure uniformly having pores at any part of the gel (hereinafter referred to as "uniform structure") is more preferable than a structure having pores only on the surface of the gel. It is preferred that a porosity of the gel is not less than 20%. The carrier may be selected from suitable shapes such as particle, fiber, sheet and hollow fiber. In case of using a carrier in the shape of particle, although a particle having a smaller size generally shows an excellent adsorbing capacity, the pressure-drop increases with an extremely small size. Therefore, a particle having a size of 1 μm to 5000 μm in diameter is preferred. Furthermore, it is preferred that a carrier has functional groups to be utilized for the immobilization of ligand or groups to be easily activated. Examples of the group are, for instance, amino, carboxyl, hydroxyl, thiol, acid anhydride, succinylimide, chlorine, aldehyde, aminde, epoxy group, and the like.

Representative examples of the water-insoluble porous hard gel used in the present invention are, for instance, a porous hard gel of a synthetic or a natural polymer such as stylene-divinylbenzene copolymer, cross-linked polyvinyl alcohol, cross-linked polyacrylate, cross-linked vinyl ether-maleic anhydride copolymer, cross-linked stylene-maleic anhydride copolymer or cross-linked polyamide, a porous cellulose gel, an inorganic porous hard gel such as silica gel, porous glass, porous alumina, porous silica alumina, porous hydroxyapatite, porous calcium silicate, porous zirconia or porous zeolite, and the like. Of course it is to be understood that the porous hard gels used in the present invention are not limited to those set forth as examples above. The surface of the above-mentioned porous hard gel may be coated with polysaccharides, synthetic polymers, and the like. These porous hard gels may be employed alone or in an admixture thereof.

In the above representative examples, some of the porous polymer hard gels composed of synthetic polymers have a fear of toxicity due to unreacted monomers and a less adsorbing capacity than that of a soft gel.

Therefore, in the above representative examples, a porous cellulose gel is one of the particularly preferable carriers for the present invention, and it satisfies the above all four points required for the carrier. In addition, the porous cellulose gel has various excellent advantages such as hydrophilicity due to being composed of cellulose, a large number of hydroxyl groups to be utilized for immobilization, less nonspecific adsorption, and sufficient adsorbing capacity not inferior to that of a soft gel due to its relatively high strength even with a large porosity. Therefore, the porous cellulose gel on which a ligand is immobilized provides a nearly ideal adsorbent.

As the porous cellulose gel used in the present invention, although cellulose per se is preferred, a cellulose derivative such as an esterified cellulose or an etherified cellulose, or a mixture of cellulose and the cellulose derivatives may be employed. Examples of the cellulose derivative are, for instance, acetyl cellulose, methyl cellulose, ethyl cellulose, carboxymethyl cellulose, and the like. It is preferred that the cellulose gel is in the spherical shape. The cellulose gel is prepared, for example, by dissolving or swelling cellulose and/or a cellulose derivatives with a solvent, dispersing the resulting mixture into another solvent being not admixed with the used solvent to make beads, and then regenerating the beads. The cellulose and/or cellulose derivatives may be cross-linked or not.

A porosity of a porous cellulose gel may be a measure of cellulose content. The cellulose content is expressed by the following formula:

$$\text{Cellulose content (\%)} = \frac{W}{Vt - Vo} \times 100$$

wherein W is dry gel weight (g), Vt is a volume of column packed with gel (ml) and Vo is a void volume (ml).

It is preferred that the cellulose content of the porous cellulose gel used in the present invention is 2% to 20%. In case of less than 2%, the mechanical strength of gel is reduced, and in case of more than 20%, the pore volume is reduced.

Representative examples of the ligand used in the present invention are as follows:

As ligands to remove VLDL and/or LDL containing a large amount of cholesterol and causing arteriosclerosis, sulfated compounds are preferred as a ligand.

As the sulfated compound used for the ligand, there may be employed a compound obtained by sulfation of a hydroxy-containing compound. Examples of the sulfated compounds are, for instance, a sulfated carbohydrate, a sulfated polyhydric alcohol, polysulfated anethol, a sulfated hydroxy-containing polymer such as polyvinyl alcohol or polyhydroxyethyl methacrylate, and the like. Typical sulfated carbohydrate is a sulfated saccharide. Examples of the saccharides are, for instance a polysaccharide, a tetrose such as threose, a pentose such as arabinose, xylose or ribose, a hexose such as glucose, galactose, mannose or fructose, a derivative thereof, a deoxysaccharide such as fucose, an amino-saccharide such as galactosamine, an acidic saccharide such as uronic acid, glucronic acid or ascorbic acid. Examples of the polyhydric alcohol are, for instance, a glycol such as ethylene glycol, glycerol, sorbite pentaerythritol, and the like. Examples of the sulfated polysaccharides are heparin, dextran sulfate, chondroitin sulfate, chondroitin poly-sulfate, heparan sulfate, keratan sulfate, xylan sulfate, caronin sulfate, cellulose sulfate, chitin sulfate, chitosan sulfate, pectin sulfate, inulin sulfate, arginine sulfate, glycogen sulfate, polylactose sulfate, carrageenan sulfate, starch sulfate, polyglucose sulfate, laminarin sulfate, galactan sulfate, levan sulfate and mepesulfate. Preferable examples of the above sulfated compounds are, for instance, sulfated polysaccharides such as heparin, dextran sulfate, chondroitin polysulfate, and/or the salts thereof, and particularly preferable examples are a dextran sulfate and/or the salt thereof. Examples of the salt of the above sulfated compound are, for instance, a water-soluble salt such as sodium salt or potassium salt, and the like.

Dextran sulfate and/or the salt thereof are explained in more detail hereinbelow.

Dextran sulfate and/or the salt thereof are sulfuric acid ester of dextran being a polysaccharide produced by *Leuconostoc mesenteroides*, etc., and/or the salt thereof. It has been known that dextran sulfate and/or the salt thereof form a precipitate with lipoproteins in the presence of a divalent cation, and dextran sulfate and/or the salt thereof having a molecular weight of about $5 \times 10^5$ (intrinsic viscosity of about 0.20 dl/g) are generally employed for this precipitation. However, as shown in the following Example 39 of Run Nos. (1) and (2), a porous hard gel on which some of the above-mentioned dextran sulfate and/or the salt thereof are immobilized is poor in affinity to VLDL and/or LDL. As a result of extensive studies to solve the above problems, it has now been found that dextran sulfate having an intrinsic viscosity of not more than 0.12 dl/g, preferably not more than 0.08 dl/g, and a sulfur content of not less than 15% by weight has high affinity and selectivity to VLDL and/or LDL. Furthermore, the adsorbent of the present invention employing such dextran sulfate and/or the salt thereof as a ligand has high affinity and selectivity even in the absence of a divalent cation. Although a toxicity of dextran sulfate and/or the salt thereof is low, the toxicity increases with increasing of molecular weight. From this point of view, the use of dextran sulfate and/or the salt thereof having an intrinsic viscosity of not more than 0.12 dl/g, preferably not more than 0.08 dl/g can prevent a danger in case that the immobilized dextran sulfate and/or the salt thereof should be released from a carrier. In addition, dextran sulfate and/or the salt thereof are less changed by a sterilizing procedure such as steam sterilization by autoclaving, because they are linked mainly by $\alpha(1\ 6)$-glycosidic linkage. Although there are various methods for measuring a molecular weight of dextran sulfate and/or the salt thereof, a method by measuring viscosity is general. Dextran sulfate and/or the salt thereof, however, show different viscosities depending on various conditions such as ion strength, pH value, and sulfur content (content of sulfonic acid group). The term "intrinsic viscosity" used in the present invention means a viscosity of sodium salt of dextran sulfate measured in a neutral 1M NaCl aqueous solution, at 25° C. The dextran sulfate and/or the salt thereof used in the present invention may be in the form of straight-chain or branched-chain.

For coupling a ligand with a carrier, various methods such as physical adsorption methods, ionic coupling methods and covalent coupling methods may be employed. In order to use the adsorbent of the present invention in extracorporeal circulation treatment, it is important that the ligand is not released. Therefore, a covalent coupling method having a strong bond between ligand and carrier is preferred. In case of employing other methods, a modification is necessary to prevent the release of ligand. If necessary, a spacer may be introduced between ligand and carrier.

It is preferred that a gel is activated by a reagent such as a cyanogen halide, epichlorohydrin, a polyoxirane compound such as bisepoxide or triazine halide, and then reacted with a ligand to give the desired adsorbent. In that case, it is preferred that a gel having a group to be activated such as hydroxyl group is employed as a carrier. In the above reagents, epichlorohydrin or a polyoxirane compound such as bisepoxide is more preferred, because a ligand is strongly immobilized on a carrier activated by using such a reagent and a release of a ligand is reduced.

Epichlorohydrin and a polyoxirane compound, however, show lower reactivity, particularly lower to dextran sulfate and/or the salt thereof, because dextran sulfate and/or the salt thereof have hydroxyl group alone as a functional group. Therefore, it is not easy to obtain a sufficient amount of immobilized ligand.

As a result of extensive studies, it has now been found that the following coupling method is preferred in case of using dextran sulfate and/or the salt thereof as a ligand. That is, a porous polymer hard gel is reacted with epichlorohydrin and/or a polyoxirane compound to introduce epoxy groups into the gel, and then dextran sulfate and/or the salt thereof is reacted with the resulting epoxy-activated gel in a concentration of not less than 3% based on the weight of the whole reaction system excluding the dry weight of the gel, more preferably not less than 10%. This method gives a good immobilizing efficiency. In that case, a porous cellulose gel is particularly suitable as a carrier.

On the other hand, when a porous inorganic hard gel is employed as a carrier, it is preferred that the gel is activated with a reagent such as an epoxysilane, e.g. $\gamma$-glycidoxypropyltrimethoxysilane or an aminosilane, e.g. $\gamma$-aminopropyltriethoxysilane, and then reacted with a ligand to give the desired adsorbent.

The amount of immobilized ligand varies depending on properties of the ligand used such as shape and activity. For sufficient removal of VLDL and/or LDL by using a polyanion compound, for instance, it is preferred that the polyanion compound is immobilized in an amount of not less than 0.02 mg/ml of an apparent column volume occupied by an adsorbent (hereinafter referred to as "bed volume"), economically 100 mg or less. The preferable range is 0.5 to 20 mg/ml of bed volume. Particularly, for removal of VLDL and/or LDL by using dextran sulfate and/or the salt thereof as a ligand, it is preferred that the amount of immobilized ligand is not less than 0.2 mg/ml of bed volume. After the coupling reaction, the unreacted polyanion compound may be recovered for reuse by purification, etc.

It is preferred that the remaining unreacted active groups are blocked by ethanolamine, and the like.

In accordance with the present invention, an adsorbent composed of porous cellulose gel having an exclusion limit of $10^6$ to $10^8$ and a particle size of 30 to 200 $\mu$m on which sodium salt of dextran sulfate having an intrinsic viscosity of not more than 0.12 dl/g and a sulfur content of not less than 15% by weight is immobilized, is particularly suitable for removal of VLDL and/or LDL in extracorporeal circulation treatment of hypercholesterolemia.

The adsorbent of the present invention may be employed for various kinds of use. Representative example of the use is extracorporeal circulation treatment performed by incorporating a column into extracorporeal circulation circuit and passing body fluid such as blood or plasma through the column, the column being packed with the adsorbent of the present invention. The use of the adsorbent is not necessarily limited to the above example.

The adsorbent of the present invention can be subjected to steam sterilization by autoclaving so long as the ligand is not largely degenerated, and this sterilization procedure does not affect on micro pore structure, particle shape and gel volume of the adsorbent.

The present invention is more specifically described and explained by means of the following Reference Examples and Examples, and it is to be understood that the present invention is not limited to the Reference Examples and Examples.

REFERENCE EXAMPLE 1

Biogel A5m (a commercially available agarose gel made by Biorad Co., particle size: 50 to 100 mesh) as a soft gel and Toyopearl HW65 (a commercially available cross-linked polyacrylate gel made by Toyo Soda Manufacturing Co., Ltd., particle size: 50 to 100 μm) and Cellulofine GC-700 (a commercially available porous cellulose gel made by Chisso Corporation, particle size: 45 to 105 μm) as a hard gel were uniformly packed, respectively, in a glass column (inner diameter: 9 mm, height: 150 mm) having filters (pore size: 15 μm) at both top and bottom of the column. Water was passed through the thus obtained column, and a relation between flow rate and pressure-drop was determined. The results are shown in FIG. 1. As shown in FIG. 1, flow rate increased approximately in proportion to increase of pressure-drop in the porous polymer hard gels. On the other hand, the agarose gel was consolidated. As a result, increasing pressure did not make flow rate increase.

REFERENCE EXAMPLE 2

Figure 2:
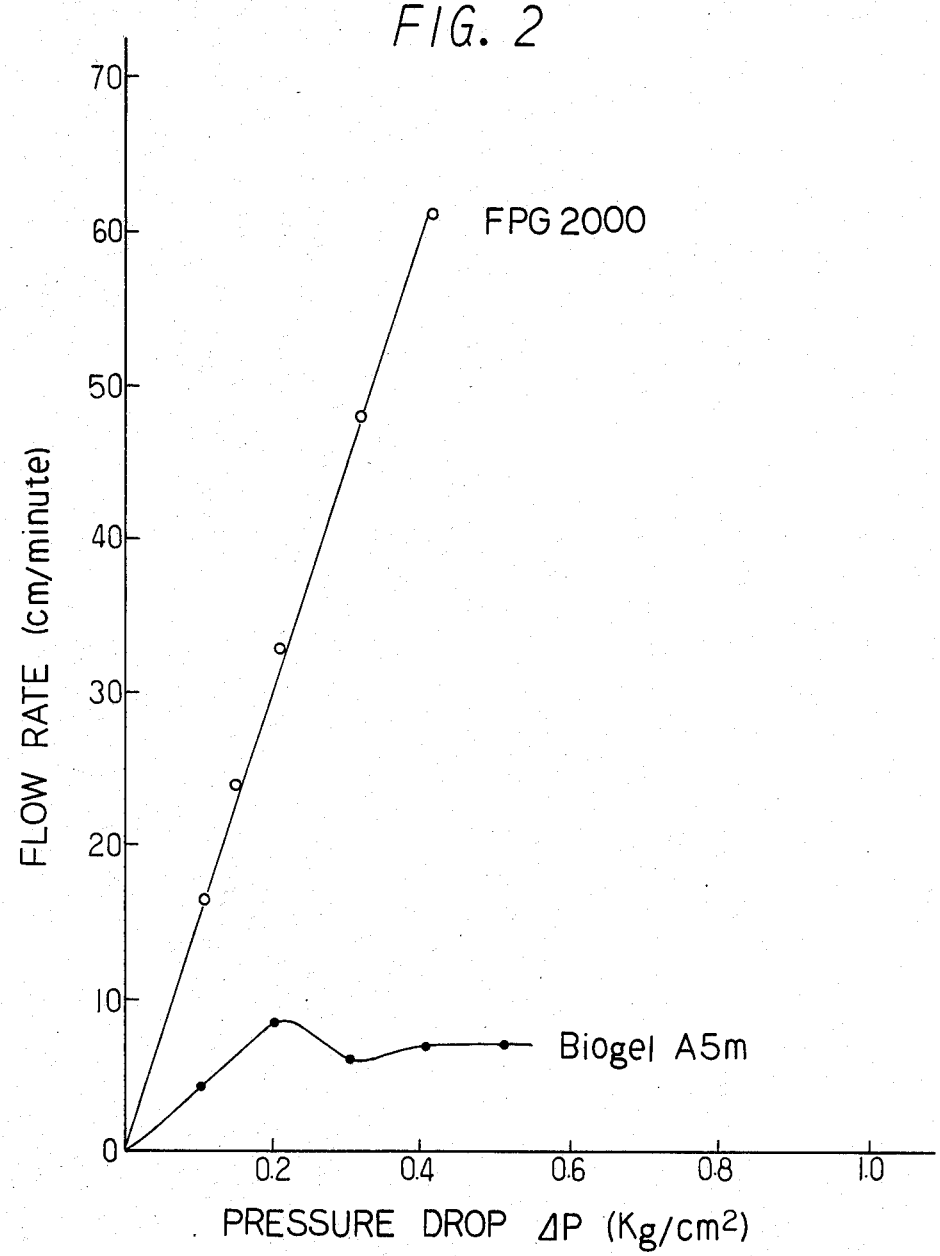

The procedures of Reference Example 1 were repeated except that FPG 2000 (a commercially available porous glass made by Wako Pure Chemical Industry Ltd., particle size: 80 to 120 mesh) instead of porous polymer hard gels was employed as a porous inorganic hard gel. The results are shown in FIG. 2. As shown in FIG. 2, flow rate increased approximately in proportion to increase of pressure-drop in the porous glass, while not in the agarose gel.

EXAMPLE 1

Toyopearl HW55 (a commercially available cross-linked polyacrylate gel made by Toyo Soda Manufacturing Co., Ltd., exclusion limit: $7 \times 10^5$, particle size: 50 to 100 μm) having a uniform structure was employed as a carrier.

To 10 ml of the gel were added 6 ml of saturated NaOH aqueous solution and 15 ml of epichlorohydrin, and the reaction mixture was subjected to reaction with stirring at 50° C. for 2 hours. The gel was washed successively with alcohol and water to introduce epoxy groups into the gel. To the resulting epoxy-activated gel was added 20 ml of concentrated aqueous ammonia, and the reaction mixture was stirred at 50° C. for 2 hours to introduce amino groups into the gel.

Three ml portion of the thus obtained activated-gel containing amino groups was added to 10 ml of aqueous solution (pH 4.5) containing 200 mg of heparin. To the resulting reaction mixture was added 200 mg of 1-ethyl-3-(dimethylaminopropyl)-carbodiimide while maintaining the reaction mixture at pH 4.5, and then the reaction mixture was shaken at 4° C. for 24 hours. After completion of the reaction, the resulting reaction mixture was washed successively with 2M NaCl aqueous solution, 0.5M NaCl aqueous solution and water to give the desired gel on which heparin was immobilized (hereinafter referred to as "heparin-gel"). The amount of immobilized heparin was 2.2 mg/ml of bed volume.

EXAMPLES 2 TO 4

The procedures of Example 1 were repeated except that Toyopearl HW60 (exclusion limit: $1 \times 10^6$, particle size: 50 to 100 μm), Toyopearl HW 65 (exclusion limit: $5 \times 10^6$, particle size: 50 to 100 μm) and Toyopearl HW75 (exclusion limit: $5 \times 10^7$, particle size: 50 to 100 μm) instead of Toyopearl HW55 were employed, respectively, to give each heparin-gel. Toyopearl HW60, Toyopearl HW65 and Toyopearl HW75 are all commercially available cross-linked polyacrylate gels having a uniform structure made by Toyo Soda Manufacturing Co., Ltd. The amounts of immobilized heparin were, respectively, 1.8 mg, 1.4 mg and 0.8 mg/ml of bed volume.

EXAMPLE 5

Cellulofine GC 700 (a commercially available porous cellulose gel made by Chisso Corporation, exclusion limit: $4 \times 10^5$, particle size: 45 to 105 μm) having a uniform structure was employed as a carrier.

The gel was filtered with suction, and 4 g of 20% NaOH and 12 g of heptane were added to 10 g of the suction-filtered gel. One drop of Tween 20 (nonionic surfactant) was further added to the reaction mixture which was stirred for dispersing the gel. After stirring at 40° C. for 2 hours, 5 g of epichlorohydrin was added to the reaction mixture which was further stirred at 40° C. for 2 hours. After the reaction mixture was allowed to stand, the resulting supernatant was discarded, and the gel was washed with water to introduce epoxy groups into the gel. To the resulting epoxy-activated gel was added 15 ml of concentrateddaqueous ammonia, and the reaction mixture was stirred at 40° C. for 1.5 hours, filtered with suction and washed with water to introduce amino groups into the gel.

Three ml portion of the thus obtained activated gel containing amino groups was added to 10 ml of aqueous solution (pH 4.5) containing 200 mg of heparin. To the resulting reaction mixture was added 200 mg of 1-ethyl-3-(dimethylaminopropyl)-carbodiimide while maintaining the reaction mixture at pH 4.5, and then the reaction mixture was shaken at 4° C. for 24 hours. After completion of the reaction, the resulting reaction mixture was washed successively with 2M NaCl aqueous solution, 0.5M NaCl aqueous solution and water to give the desired heparin-Cellulofine A-3. The amount of immobilized heparin was 2.5 mg/ml of bed volume.

EXAMPLES 6 TO 7

The procedures of Example 5 were repeated except that Cellulofine A-2 (exclusion limit: $7\times10^5$, particle size: 45 to 105 $\mu$m) and Cellulofine A-3 (exclusion limit: $5\times10^7$, particle size: 45 to 105 $\mu$m) instead of Cellulofine GC 700 were employed, respectively, to give each heparin-gel. Both Cellulofine A-2 and Cellulofine A-3 are commercially available porous cellulose gels having a uniform structure made by Chisso Corporation. The amounts of immobilized heparin were, respectively, 2.2 mg and 1.8 mg/ml of bed volume.

EXAMPLE 8

The procedures of Example 5 were repeated except that Cellulofine A-3 having a particle size of 150 to 200 $\mu$m instead of 45 to 105 $\mu$m was employed. The amount of immobilized heparin was 1.5 mg/ml of bed volume.

EXAMPLE 9

The procedures of Example 1 were repeated except that Toyopearl HW65 instead of Toyopearl HW55 and chondroitin polysulfate instead of heparin were employed, to give the desired chondroitin polysulfate-Toyopearl HW65. The amount of immobilized chondroitin polysulfate was 1.2 mg/ml of bed volume.

EXAMPLE 10

To 4 ml of Cellulofine A-3 was added water to make the volume up to 10 ml, and then 0.5 mole of $NaIO_4$ was added. After stirring at a room temperature for one hour, the reaction mixture was washed with water by filtration to introduce aldehyde groups into the gel. The thus obtained gel was suspended in 10 ml of phosphate buffer of pH 8 and stirred at a room temperature for 20 hours after addition of 50 mg of ethylenediamine. The gel was filtered off and then suspended in 10 ml of 1% $NaBH_4$ solution. After reducing reaction for 15 minutes, the reaction mixture was filtered and washed with water to introduce amino groups into the gel.

In 10 ml of 0.25M $NaIO_4$ solution was dissolved 300 mg of sodium salt of dextran sulfate. After stirring at a room temperature for 4 hours, 200 mg of ethylene glycol was added to the resulting solution and stirred for one hour. The resulting solution was adjusted to pH 8, and then the above gel containing amino groups was suspended in the solution and stirred for 24 hours. After completion of the reaction, the gel was filtered, washed with water, and then suspended in 10 ml of 1% $NaBH_4$ solution. The resulting suspension was subjected to reducing reaction for 15 minutes and washed with water by filtration to give the desired sodium salt of dextran sulfate-Cellulofine A-3. The amount of immobilized sodium salt of dextran sulfate was 0.5 mg/ml of bed volume.

EXAMPLE 11

Cellulofine A-3 was treated in the same manner as in Example 5 to introduce epoxy groups into the gel.

Two ml of the thus obtained epoxy-activated gel was added to 2 ml of aqueous solution containing 0.5 g of sodium salt of dextran sulfate (intrinsic viscosity 0.055 dl/g, average polymerization degree: 40, sulfur content: 19% by weight), and the reaction mixture was adjusted to pH 12. The concentration of sodium salt of dextran sulfate was about 10% by weight. The resulting reaction mixture was filtered and washed successively with 2M NaCl aqueous solution, 0.5M NaCl aqueous solution and water to give the desired sodium salt of dextran sulfate-Cellulofine A-3. The remaining unreacted epoxy groups were blocked with monoethanolamine. The amount of immobilized sodium salt of dextran sulfate was 1.5 mg/ml of bed volume.

EXAMPLE 12

To 5 g of suction-filtered Cellulofine A-3 were added 2.5 ml of 1,4-butanediol diglycidyl ether and 7.5 ml of 0.1N NaOH aqueous solution, and the reaction mixture was stirred at a room temperature for 18 hours to introduce epoxy groups into the gel.

The thus obtained epoxy-activated gel was reacted with sodium salt of dextran sulfate in the same manner as in Example 11 to give the desired sodium salt of dextran sulfate-Cellulofine A-3. The amount of immobilized sodium salt of dextran sulfate was 1.8 mg/ml of bed volume.

EXAMPLE 13

The procedures of Example 11 were repeated except that Cellulofine A-6 (a commercially available porous cellulose gel made by Chisso Corporation, exclusion limit: $1\times10^8$, particle size: 45 to 105 $\mu$m) having a uniform structure instead of Cellulofine A-3 was employed to give the desired sodium salt of dextran sulfate-Cellulofine A-6. The amount of immobilized sodium salt of dextran sulfate was 1.2 mg/ml of bed volume.

EXAMPLE 14

Toyopearl HW65 was treated in the same manner as in Example 1 to introduce epoxy groups into the gel.

Two ml of the thus obtained epoxy-activated gel was treated in the same manner as in Example 11 to give the desired sodium salt of dextran sulfate-Toyopearl HW65. The amount of immobilized sodium salt of dextran sulfate was 0.4 mg/ml of bed volume.

EXAMPLE 15

FPG 2000 (exclusion limit: $1\times10^9$, particle size: 80 to 120 mesh, average pore size: 1950 Å) was heated in diluted nitric acid for 3 hours. After washing and drying, the gel was heated at 500° C. for 3 hours and then refluxed in 10% $\gamma$-aminopropyltriethoxysilane solution in toluene for 3 hours. After washing with methanol, a $\gamma$-aminopropyl-activated glass was obtained.

Two g of the thus obtained activated glass was added to 10 ml of aqueous solution (pH 4.5) containing 200 mg of heparin. The reaction mixture was treated in the same manner as in Example 1 to give the desired heparin-FPG 2000. The amount of immobilized heparin was 1.2 mg/ml of bed volume.

EXAMPLES 16 TO 18

The procedures of Example 15 were repeated except that FPG 700 (a commercially available porous glass made by Wako Pure Chemical Industry Ltd., exclusion limit: $5\times10^7$, particle size: 80 to 120 mesh, average pore size: 70 Å), FPG 1000 (a commercially available porous glass made by Wako Pure Chemical Industry Ltd., exclusion limit: $1\times10^8$, particle size: 80 to 120 mesh, average pore size: 1091 Å) and Lichrospher Si4000 (a commercially available porous silica gel made by Merck & Co. Inc., exclusion limit: $1\times10^9$, average particle size: 10 $\mu$m, average pore size: 4000 Å) instead of FPG 2000 were employed. The amounts of immobilized heparin were, respectively, 3.2 mg, 2.2 mg and 0.5 mg/ml of bed volume.

EXAMPLE 19

The procedures of Example 15 were repeated except that chondroitin polysulfate instead of heparin was employed to give the desired chondroitin polysulfate-FPG 2000. The amount of immobilized chondroitin polysulfate was 1.0 mg/ml of bed volume.

EXAMPLE 20

FPG 2000 was treated in the same manner as in Example 15 to introduce γ-aminopropyl groups into the gel. The thus obtained activated gel was reacted with sodium salt of dextran sulfate in the same manner as in Example 10 to give the desired sodium salt of dextran sulfate-FPG 2000. The amount of immobilized sodium salt of dextran sulfate was 0.5 mg/ml of bed volume.

EXAMPLE 21

FPG 2000 was refluxed in 10% solution of γ-glycidoxypropyltrimethoxysilane for 3 hours and then washed with methanol. The thus obtained activated gel was reacted with sodium salt of dextran sulfate in the same manner as in Example 11 except that the reaction was carried out at pH 8.5 to 9 and at 45° C. to give the desired sodium salt of dextran sulfate-FPG 2000.

EXAMPLE 22

The procedures of Example 11 were repeated except that sodium salt of glucose sulfate instead of dextran sulfate was employed to give the desired sodium salt of glucose sulfate-Cellulofine A-3.

The amount of immobilized sodium salt of glucose was 1.0 mg/ml of bed volume.

EXAMPLE 23

The procedures of Example 11 were repeated except that sodium salt of polyvinyl alcohol sulfate instead of dextran sulfate was employed to give the desired sodium salt of polyvinyl alcohol sulfate-Cellulofine A-3.

The amount of immobilized sodium salt of polyvinyl alcohol sulfate was 1.5 mg/ml of bed volume.

TEST EXAMPLE 1

Each adsorbent obtained in Examples 1 to 23 was uniformly packed in a column (internal volume: about 3 ml, inner diameter: 9 mm, height: 47 mm) and 18 ml of plasma containing 200 U of heparin was passed through the column at a flow rate of 0.3 ml/minute with varying the plasma origins depending on the kind of the desired substance to be removed. That is, human plasma derived from familial hypercholesterolemia, normal human plasma, normal human plasma containing about 100 μg/ml of a commercially available endotoxin, human plasma derived from rheumatism, human plasma derived from systemic lupus erythematosus and human plasma derived from myasthenia gravis were used, respectively, for the tests of removing VLDL and/or LDL; IgG, $C_{1q}$ or haptoglobin; endotoxin; rheumatoid factor; anti-DNA antibody or DNA; and anti-acetylcholine receptor antibody. The pressure-drop in the column was 15 mmHg or less throughout the test period and no crogging was observed. In each adsorbent, LDL, VLDL, HDL, total protein in plasma which was passed through the column was determined to obtain a removal efficiency. The results are summarized in Table 1.

TABLE 1

| Example No. | Ligand | Carrier | Coupling method | Removal rate (%) | | |
|---|---|---|---|---|---|---|
| | | | | LDL + VLDL | HDL | Protein*[1] |
| 1 | Heparin | Toyopearl HW55 | Epichlorhydrin-ammonia | 23 | 5 | 2 |
| 2 | Heparin | Toyopearl HW60 | Epichlorhydrin-ammonia | 31 | 11 | 3 |
| 3 | Heparin | Toyopearl HW65 | Epichlorhydrin-ammonia | 54 | 12 | 3 |
| 4 | Heparin | Toyopearl HW75 | Epichlorhydrin-ammonia | 51 | 8 | 4 |
| 5 | Heparin | Cellulofine GC-700 | Epichlorhydrin-ammonia | 15 | 0 | 3 |
| 6 | Heparin | Cellulofine A-2 | Epichlorhydrin-ammonia | 26 | 2 | 2 |
| 7 | Heparin | Cellulofine A-3 (particle size: 45 to 105 μm) | Epichlorhydrin-ammonia | 56 | 2 | 3 |
| 8 | Heparin | Cellulofine A-3 (particle size: 150 to 200 μm) | Epichlorhydrin-ammonia | 55 | 3 | 2 |
| 15 | Heparin | FPG 2000 | amminosilane | 57 | 13 | 8 |
| 16 | Heparin | FPG 700 | amminosilane | 16 | 8 | 7 |
| 17 | Heparin | FPG 1000 | amminosilane | 28 | 9 | 9 |
| 18 | Heparin | Lichrosphere Si 4000 | amminosilane | 24 | 5 | 14 |
| 9 | Chondroitin polysulfate | Toyopearl HW65 | Epichlorhydrin-ammonia | 46 | 12 | 9 |
| 19 | Chondroitin polysulfate | FPG 2000 | aminosilane | 45 | 15 | 13 |
| 22 | glucose sulfate | Cellulofine A-3 | Epichlorhydrin | 38 | 5 | 2 |
| 23 | polyvinyl alcohol sulfate | Cellulofine A-3 | Epichlorhydrin | 47 | 3 | 2 |
| 10 | sodium salt of dextran sulfate | Cellulofine A-3 | $NaIO_4$—diamine | 38 | 2 | 2 |
| 20 | sodium salt of dextran sulfate | FPG 2000 | $NaIO_4$—diamine | 37 | 12 | 4 |
| 11 | sodium salt of dextran sulfate | Cellulofine A-3 | Epichlorhydrin | 50 | 3 | 1 |

TABLE 1-continued

| Example No. | Ligand | Carrier | Coupling method | Removal rate (%) LDL + VLDL | HDL | Protein*[1] |
|---|---|---|---|---|---|---|
| 12 | sodium salt of dextran sulfate | Cellulofine A-3 | Bisepoxide | 65 | 3 | 2 |
| 13 | sodium salt of dextran sulfate | Cellulofine A-6 | Epichlorhydrin | 60 | 3 | 2 |
| 14 | sodium salt of dextran sulfate | Toyopearl HW65 | Epichlorhydrin | 42 | 5 | 5 |
| 21 | sodium salt of dextran sulfate | FPG 2000 | Epoxysilane | 60 | 8 | 11 |

*[1]Protein other than lipoprotein, i.e. total protein - lipoprotein.

EXAMPLE 24

[Effects of intrinsic viscosity and sulfur content of dextran sulfate and/or the salt thereof]

Cellulofine A-3 was treated in the same manner as in Example 5 to introduce epoxy groups into the gel. The thus obtained epoxy-activated gel was reacted with each sodium salt of dextran sulfate having the intrinsic viscosity and sulfur content shown in the following Table 2 (Run Nos. (1) to (7)) in the same manner as in Example 11.

One ml portion of the resulting each adsorbent was packed in a column, and then 6 ml of human plasma containing 300 mg/dl of total cholesterol derived from a familial hypercholesterolemia patient was passed through the column at a flow rate of 0.3 ml/minute. The removal efficiency for LDL was determined from the amount of adsorbed LDL measured by using the total amount of cholesterol as an indication. That is, the amount of cholesterol in the human plasma used was mostly derived from LDL. The results are shown in Table 2.

TABLE 2

| Run No. | Intrinsic viscosity (dl/g) | Sulfur content (% by weight) | Concentration of sodium salt of dextran sulfate in the reaction system (% by weight) | Amount of immobilized sodium salt of dextran sulfate (mg/ml of bed volume) | Removal efficiency (%) |
|---|---|---|---|---|---|
| (1) | 0.20 | 17.7 | about 10 | 4.2 | 18 |
| (2) | 0.124 | 5.7 | " | 2.5 | 17 |
| (3) | 0.027 | 17.7 | " | 2 | 62 |
| (4) | 0.055 | 19.0 | " | 1.5 | 50 |
| (5) | 0.083 | 19.2 | " | 4.0 | 44 |
| (6) | 0.118 | 17.7 | " | 4.3 | 39 |
| (7) | 0.055 | 19.0 | 2.5 | 0.15 | 32 |

EXAMPLE 25

[Effect of amount of epoxy group introduced]

Toyopearl 65 was treated in the same manner as in Example 1 to introduce epoxy groups into the gel and CSKA-3 (a cmmercially available porous cellulose gel made by Chisso Corporation, exclusion limit: 5×10^7, particle size: 45 to 105 μm) having a uniform structure was treated in the same manner as in Example 5 to introduce epoxy groups into the gel. The amounts of epoxy groups introduced were, respectively, 250 μmoles and 30 μmoles/ml of bed volume.

Each gel was reacted with sodium salt of dextran sulfate (intrinsic viscosity: 0.027 dl/g, sulfur content: 17.7% by weight) in the same manner as in Example 11 except that the concentration of sodium salt of dextran sulfate based on the weight of the whole reaction system excludig the dry weight of the gel was charged.

The thus obtained adsorbent was subjected to the determination of removal efficiency for LDL in the same manner as in Example 24. The results are summarized in Table 3.

TABLE 3

| Carrier | Amount of epoxy group introduced (μmole/ml of bed volume) | Amount of immobilized sodium salt of dextran sulfate mg/ml of bed volume | Amount of immobilized sodium salt of dextran sulfate μg/μmole of epoxy group | Concentration of sodium salt of sulfate (% by weight) | Removal efficiency (%) |
|---|---|---|---|---|---|
| Toyopearl HW65 | 250 | 0.4 | 1.6 | 13 | 40 |
| CSKA-3 | 30 | 0.15 | 5 | 2.5 | 36 |
| " | 30 | 2.3 | 76 | 13 | 63 |

EXAMPLE 26

One ml portion of the adsorbent obtained in Example 24 of Run No. (3) was uniformly packed in a column having an internal volume of 1 ml, and 6 ml of normal human plasma containing LDL and HDL cholesterol in the ratio of approximately 1:1 was passed through the column. LDL in the plasma passed through the column was greatly reduced, while HDL was scarcely reduced.

EXAMPLE 27

Figure 3:
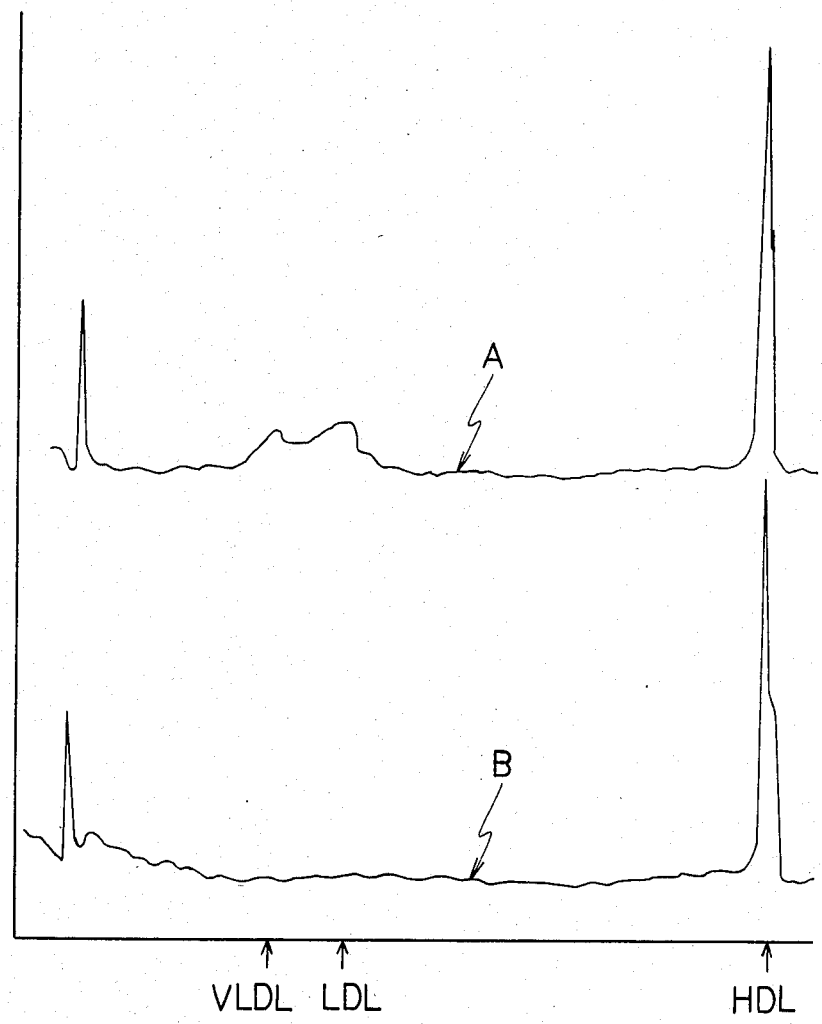
FIG. 3 is a chart of polyacrylamide disc gel electrophoresis obtained in Example 27.

One ml portion of the adsorbent obtained in Example 24 of Run No. (3) was uniformly packed in a column having an internal volume of 1 ml, and 6 ml of normal rabbit plasma containing lipoproteins of VLDL, LDL and HDL was passed through the column. The plasma obtained before and after the column treatment were, respectively, examined by polyacrylamide disc gel electrophoresis. The results are shown in FIG. 3. In FIG. 3, curves A and B show, respectively, the results obtained before and after the column treatment. The axis of ordinates indicates the absorbance at 570 nm and the axis of abscissas indicates the migration positions at which bands of VLDL, LDL and HDL were, respectively appeared.

As shown in FIG. 3, VLDL and LDL were significantly adsorbed, while HDL was not.

EXAMPLE 28

The adsorbents obtained in Examples 1 to 7 and 11 to 14 were sterilized in an autoclave at 120° C. for 15 minutes. Each resulting sterilized adsorbent was subjected to the determination of removal efficiency for LDL in the same manner as in Test Example 1. As a result, the removal efficiencies were not inferior to those obtained without sterilizing by autoclaving. In addition, pressure-drop was not changed.

What we claim is:

1. An adsorbent for removing low and/or very low density lipoprotein from body fluid in extracorporeal circulation treatment, which comprises a water-insoluble porous hard gel with exclusion limit of $10^6$ to $10^9$ daltons on which a sulfated compound is immobilized by a covalent linkage; said sulfated compound being a compound obtained by sulfation of a hydroxy-containing compound.

2. The adsorbent of claim 1, wherein said water-insoluble porous hard gel is a water-insoluble porous polymer hard gel.

3. The adsorbent of claim 2, wherein said water-insoluble porous polymer hard gel is a porous cellulose gel.

4. The adsorbent of claim 1, wherein said water-insoluble porous hard gel is a porous inorganic hard gel.

5. The adsorbent of claim 4, wherein said water-insoluble inorganic hard gel is a member selected from the group consisting of porous glass, porous silica gel and porous alumina.

6. The adsorbent of claim 1, wherein the sulfated compound is a sulfated carbohydrate.

7. The adsorbent of claim 6, wherein the sulfated carbohydrate is a sulfated saccharide.

8. The adsorbent of claim 7, wherein the sulfated saccharide is a sulfated polysaccharide.

9. The adsorbent of claim 8, wherein the sulfated polysaccharide is a member selected from the group consisting of heparin, dextran sulfate, condroitin sulfate and salts thereof.

10. The adsorbent of claim 9, wherein the dextran sulfate, a salt thereof or a mixture of the dextran sulfate and the salt has an intrinsic viscosity of not more than 0.12 dl/g and a sulfer content of not less than 15% by weight.

11. The adsorbent of claim 1, wherein the sulfated compound is a sulfated polyhydric alcohol.

12. The adsorbent of claim 1, wherein the exclusion limit is $10^6$ to $10^8$ daltons.

13. The adsorbent of claim 1, wherein said sulfated compound is immobilized in an amount of 0.02 to 100 mg/ml of bed volume.

14. The adsorbent of claim 13, wherein the sulfated compound is immobilized in an amount of not less than 0.2 mg/ml of bed volume.

15. A process of preparing an adsorbent for removing low and/or very low density lipoprotein from body fluid in extracorporeal circulation treatment comprising a water-insoluble porous hard gel with exclusion limit of $10^6$ to $10^9$ daltons on which a sulfated compound is immobilized, wherein said water-insoluble porous hard gel is reacted with epichlorhydrin or a polyoxirane compound to introduce epoxy groups on to the gel, and then the resulting epoxy-activated gel is reacted with the sulfated compound; said sulfated compound being a compound obtained by sulfation of a hydroxy-containing compound.

16. The process of claim 15, wherein said water-insoluble hard gel is a water-insoluble porous polymer hard gel.

17. The process of claim 16, wherein said water-insoluble porous polymer hard gel is a porous cellulose gel.

18. The process of claim 15, wherein said sulfated compound is dextran sulfate, a salt thereof or a mixture of the dextran sulfate and the salt; said dextran sulfate, the salt thereof or the mixture of the dextran sulfate and the salt being reacted with the epoxy-activated gel in a concentration of not less than 3% by weight based on the weight of the whole reaction system excluding the dry weight of the porous hard gel.

19. The process of claim 18, wherein the porous hard gel is a porous cellulose gel.

* * * * *